United States Patent [19]

Schneider et al.

[11] 4,117,006
[45] Sep. 26, 1978

[54] SELECTIVE CHLORINATION OF BENZOYL CHLORIDE

[75] Inventors: Louis Schneider, Elizabeth; David E. Graham, Westfield, both of N.J.

[73] Assignee: GAF Corporation, New York, N.Y.

[21] Appl. No.: 806,378

[22] Filed: Jun. 14, 1977

[51] Int. Cl.² ............................................ C07C 51/58
[52] U.S. Cl. ............................................... 260/544 D
[58] Field of Search ................................... 260/544 D

[56] References Cited

U.S. PATENT DOCUMENTS 3,996,274  12/1976  Jurewicz ......................... 260/544 D

*Primary Examiner*—Gerald A. Schwartz
*Attorney, Agent, or Firm*—Walter C. Kehm; Walter Katz

[57] ABSTRACT

The novel process of the invention comprises selectively chlorinating benzoyl chloride in the absence of a solvent to about 7–8% unconverted benzoyl chloride, and recovering the resultant 3-chlorobenzoyl chloride in high yield from the reaction product mixture. A feature of the process is that the ratio of 3-chlorobenzoyl chloride to 2,5-dichlorobenzoyl chloride by-product is maximized.

1 Claim, 1 Drawing Figure

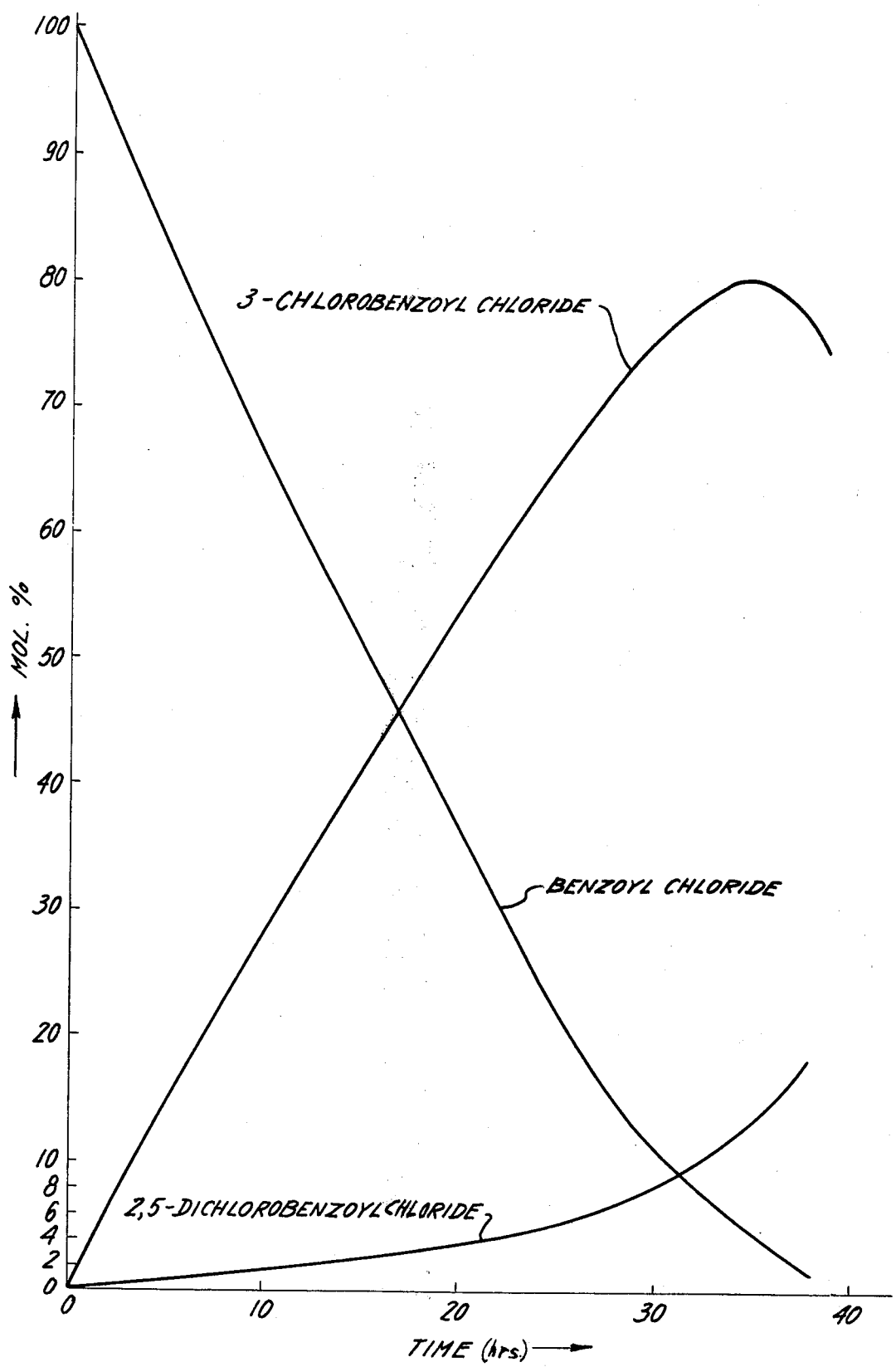

SELECTIVE CHLORINATION OF BENZOYL CHLORIDE

BACKGROUND OF THE INVENTION

1. Field of the Invention

This invention relates to the chlorination of benzoyl chloride, and, more particularly, it is concerned with a novel process for producing 3-chlorobenzoyl chloride in high selectivity in the absence of a solvent.

2. Description of the Prior Art

In U.S. Pat. No. 3,816,526, there is described a process for halogenating benzoyl chloride in the presence of anhydrous ferric chloride and iodine catalyst in carbon tetrachloride solvent to provide 3-chlorobenzoyl chloride. However, in this process, 13% or more of the benzoyl chloride remained unconverted at the conclusion of the process. Furthermore, significant amounts of dichlorobenzoyl chlorides of undefined purity were obtained. In addition, the process is expensive because the solvent must be recovered and recycled, and because the capacity of a given batch is reduced by the amount of solvent used.

In an article in the Journal of the Chemical Society 121, 251 (1922), the catalytic halogenation of benzoyl chloride in the absence of a solvent gave only a 65% yield of 3-chlorobenzoyl chloride, while 13.5% benzoyl chloride remained unconverted, and large amounts of undesirable by-products were formed.

Accordingly, it is an object of the present invention to provide an improved process for selectively chlorinating benzoyl chloride in the absence of a solvent. More particularly, it is the object of this invention to provide a process which accomplishes the following simultaneously.

1. Maximizes the yield of 3-chlorobenzoyl chloride.
2. Maximizes the ratio of 3-chlorobenzoyl chloride to 2,5-dichlorobenzoyl chloride by-product.
3. Minimizes the amount of unconverted benzoyl chloride.
4. Provides the above without the use of a solvent.

SUMMARY OF THE INVENTION

The novel process of the invention comprises selectively chlorinating benzoyl chloride in the absence of a solvent to about 7-8% unconverted benzoyl chloride, and recovering the resultant 3-chlorobenzoyl chloride in high yield from the reaction product mixture. A feature of the process is that the ratio of 3-chlorobenzoyl chloride to 2,5-dichlorobenzoyl chloride by-product is maximized.

DETAILED DESCRIPTION OF THE INVENTION

In the Drawing

The FIGURE is a graph of mole percent benzoyl chloride, 3-chlorobenzoyl chloride and 2,5-dichlorobenzoyl chloride vs. time, for the selective chlorination process of the invention.

DESCRIPTION OF THE PREFERRED EMBODIMENTS

The selective chlorination process of the invention, per se, comprises contacting benzoyl chloride with chlorine, in the absence of a solvent, and in the presence of a Friedal-Craft catalyst, at a suitable reaction temperature. Usually the catalyst is anhydrous ferric chloride and iodine, and the reaction is carried out at room temperature. Preferably, the anhydrous ferric chloride is present in an amount of about 0.3%, and the iodine about 0.04%, based on the weight of benzoyl chloride, although other concentrations may be used as well.

Referring now to the FIGURE, it is seen that initially chlorination produces the desired product, 3-chlorobenzoyl chloride, and small amounts of the major by-product of the chlorination, namely, 2,5-dichlorobenzoyl chloride. Minor amounts of other monochlorinated by-products, such as the 2-chloro, and other di- and trichloro by-products, also are formed, but these are not included herein.

As chlorination proceeds, the concentration of benzoyl chloride decreases, and the yield of 3-chlorobenzoyl chloride increases as shown in the graph; the yield of the 3-chloro product is at a maximum when the concentration of unconverted benzoyl chloride reaches a level of about 7-8 mole %. Upon further chlorination, the 3-chloro itself reacts to form the undesired 2,5-dichloro, and its yield decreases. Furthermore, at this stage in the chlorination, the 2,5-dichloro begins to increase substantially because it is formed from two monochloro sources, that is, both the 3-chloro and the 2-chloro compounds.

At 7-8 mole % unconverted benzoyl chloride, therefore, both the yield of the 3-chloro product, (about 80%), and the ratio of 3-chloro to 2,5-dichloro, are maximized.

After the chlorination, the desired 3-chlorobenzoyl chloride is recovered from the reaction product mixture. Preferably, products are recovered in two distillation steps. The first is a simple distillation at a low temperature and at a low pressure. During simple distillation, the liquid products are separated from the catalyst rapidly so that unwanted condensation reactions are minimized. The second distillation is a fractional distillation of the distillate to provide the 3-chloro and 2,5-dichloro products isolated from each other.

The preferred embodiment of the invention will be illustrated in the following example.

EXAMPLE

Charged into a 1 l, 4-necked flask equipped with a condenser, thermometer, agitator, gas inlet and outlet adapters, cooling bath, bubblers and traps are:

859.4 g, benzoyl chloride (6.11 mole)

2.67 g. anhydrous ferric chloride (0.31%, based on benzoyl chloride)

0.38 g. iodine (0.045%, based on benzoyl chloride)

Chlorine (510.5 g., 7.20 mole) is bubbled through the reaction medium at 25° C ± 1° for 35 hours to achieve a 93% conversion of benzoyl chloride to chlorinated products (see table below).

The reaction product mixture then is subjected to simple distillation through a short path (6") condenser for 6 hours at a pot temperature of 93°-126° C., and a vapor temperature of 66°-67° C., at 1-2 pressure. The residue from this simple distillation, containing the catalyst, weighed 8.4 g.

The distillate then is fractionally distilled (20% takeoff) using a 35 plate Oldershaw column to provide the desired 3-chlorobenzoyl chloride in essentially pure form, as shown in the table.

TABLE

GAS CHROMATOGRAPHIC ANALYSIS OF SELECTIVE CHLORINATION AND DISTILLATE PRODUCTS

| Sample | Weight (g.) | Benzoyl Chloride | 3-Chloro Benzoyl Chloride | 2,5-Dichloro Benzoyl Chloride |
|---|---|---|---|---|
| Reaction Product After Chlorination | 1082 | 7.13 | 78.45 | 10.31 |
| Distillate After Simple Distillation Maincut Distillate | 1064 | 8.56 | 71.65 | 12.49 |
| After Fractional Distillation | 703.9 | 0.2 | 98.51 | |

While the invention has been illustrated by reference to certain preferred embodiments thereof, it will be understood that certain changes and modifications may be made which are within the skill of the art.

We claim:

1. A process for the selective chlorination of benzoyl chloride comprising:
   (a) chlorinating benzoyl chloride, in the absence of a solvent, and in the presence of a catalyst, to about 7-8 mole % unconverted benzoyl chloride, thereby to form a monochlorinated product which is substantially the 3-chlorobenzoyl chloride in high yield, and 2,5-dichlorobenzoyl chloride as a by-product, and
   (b) recovering the 3-chlorobenzoyl chloride in essentially pure form and in high yield from the catalyst and 2,5-dichlorobenzoyl chloride present in the reaction product mixture by simple distillation at low temperature and pressure to separate rapidly liquid products from catalyst followed by fractional distillation to separate the 3-benzoyl chloride from 2,5-dichlorobenzoyl chloride.

* * * * *